United States Patent
Wismueller et al.

(10) Patent No.: US 9,733,167 B2
(45) Date of Patent: Aug. 15, 2017

(54) METHOD AND DEVICE FOR PRESERVING AND IMAGING SPECIMENS WHILE RETAINING INFORMATION ON THE SPATIAL ORIENTATION OF SPECIMENS WITH RESPECT TO REFERENCE OBJECTS

(71) Applicants: Axel Wismueller, Rochester, NY (US); Andrzej Krol, Fayetteville, NY (US); Avice O'Connell, Rochester, NY (US)

(72) Inventors: Axel Wismueller, Rochester, NY (US); Andrzej Krol, Fayetteville, NY (US); Avice O'Connell, Rochester, NY (US)

(73) Assignees: University of Rochester, Rochester, NY (US); The Research Foundation for the State University of New York, Syracuse, NY (US)

( * ) Notice: Subject to any disclaimer, the term of this patent is extended or adjusted under 35 U.S.C. 154(b) by 52 days.

(21) Appl. No.: 14/398,708

(22) PCT Filed: May 6, 2013

(86) PCT No.: PCT/US2013/039721
§ 371 (c)(1),
(2) Date: Nov. 3, 2014

(87) PCT Pub. No.: WO2013/166497
PCT Pub. Date: Nov. 7, 2013

(65) Prior Publication Data
US 2015/0083893 A1 Mar. 26, 2015

Related U.S. Application Data

(60) Provisional application No. 61/642,920, filed on May 4, 2012.

(51) Int. Cl.
*G01N 33/483* (2006.01)
*G01N 1/36* (2006.01)
*G01N 23/04* (2006.01)

(52) U.S. Cl.
CPC ............... *G01N 1/36* (2013.01); *G01N 23/04* (2013.01); *G01N 33/4833* (2013.01); *G01N 2223/307* (2013.01); *G01N 2223/6126* (2013.01)

(58) Field of Classification Search
CPC .............................. G01N 1/36; G01N 33/483
(Continued)

(56) References Cited

U.S. PATENT DOCUMENTS

| 7,227,630 B1 | 6/2007 | Zavislan |
| 8,452,374 B2 * | 5/2013 | Ma .......................... A61B 5/064 378/208 |

FOREIGN PATENT DOCUMENTS

| SU | 540190 A1 | 2/1977 |
| SU | 540190 A1 | 2/1977 |

* cited by examiner

*Primary Examiner* — Que T Le
(74) *Attorney, Agent, or Firm* — Laurence J. Hyman; Hyman IP Law

(57) ABSTRACT

An object, such as a tumor from a breast lumpectomy, is placed into an object positioning device that can hold the object without deforming it. Such a device can include a container with a deformable foam, gel, or other material. The object positioning device is moved into an imaging device. Images of the object within the object positioning device are acquired by the imaging device. The acquired images are stored, processed, or output on a display device. Information about the spatial orientation of the object with respect to a reference object is preserved.

44 Claims, 3 Drawing Sheets

(58) Field of Classification Search
USPC .................. 250/239, 208.1, 363.02–363.04, 250/370.08–370.1; 600/407–426; 128/845, 846
See application file for complete search history.

FIG. 1A

External container: can be opened, e.g. using hinges

METHOD AND DEVICE FOR PRESERVING AND IMAGING SPECIMENS WHILE RETAINING INFORMATION ON THE SPATIAL ORIENTATION OF SPECIMENS WITH RESPECT TO REFERENCE OBJECTS

REFERENCE TO RELATED APPLICATION

The present application claims the benefit of U.S. Provisional Patent Application No. 61/642,920, filed May 4, 2012, whose disclosure is hereby incorporated by reference in its entirety into the present disclosure.

FIELD OF THE INVENTION

The present invention is directed to a method and device for preserving and imaging an object, such as a breast biopsy specimen, and more particularly to such a method and device in which the spatial orientation of the object is not distorted.

DESCRIPTION OF RELATED ART

A biopsy is the medical removal of tissue from a living subject to determine the presence or extent of a disease, e.g., cancer. Once the tissue is removed, it can be studied in various ways, e.g., under a microscope, chemically, or through an imaging modality such as computed tomography. A biopsy of a discrete lump, which may also include some surrounding tissue, is called a lumpectomy.

Breast cancer is the second leading cause of cancer death in women in the United States. Over 200,000 women are diagnosed with breast cancer each year, and about 20% die from the disease. Lumpectomy is associated with a higher risk of developing a local recurrence of the cancer, which is then treated by a second surgery of either mastectomy or another lumpectomy. With current technology and procedure, the re-excision rate in lumpectomy is greater than 25%, resulting in approximately 55,000 re-excisions per year. The number of individuals affected by the flaws in lumpectomy surgeries suggests a need for improvement in the process. In addition to the added suffering of those affected, second surgeries also result in a loss of over 200 million dollars a year.

Currently, during the lumpectomy surgery, the surgeons typically excise the tumor with a rim of healthy tissue around it. That specimen is then transferred to a mobile digital radiography system, such as the PiXarray 100. The technician generally takes two images of the tissue: a horizontal image and an orthogonal image. Those two images are electronically transferred to the radiology department for radiologists to evaluate the specimen margins. The radiologist then reports back to the surgeon, ideally before the surgeon closes the surgical incision. However, the current technology involved in this step of the surgery has several deficiencies, such as (1) unclear directional markers in relation to the tissue, (2) inability to preserve the tissue geometry and (3) inability to specifically mimic in vivo orientation. Those factors contribute to ineffective communication between the radiologists and surgeons and large mechanical deformation of the specimen before imaging.

SUMMARY OF THE INVENTION

A need therefore exists in the art to minimize tissue deformation in the specimen and to maintain tissue integrity, geometry and in vivo orientation with respect to patient anatomy.

It is therefore an object of the invention to preserve histological integrity of a tissue specimen.

It is another object of the invention in at least some embodiments to keep the specimen in a sterile environment.

It is another object of the invention to preserve the spatial orientation of the tissue chunk excised during lumpectomy (or other surgery) relative to the spatial orientation of the tissue chunk as it was within the patient.

It is another object of the invention to minimize deformation of the specimen due to gravity and compression.

It is another object of the invention to minimize effects of the material surrounding the specimen with regards to effects interfering with imaging of the specimen, such as x-ray-attenuation, x-ray phase shift, or generation of MRI artifacts.

It is another object of the invention to provide fiducial markers visible in projection x-ray radiography, micro-CT, phase-contrast CT, or MRI that will define spatial orientation, specifically with regards to patient anatomy, but will not create image artifacts.

It is another object of the invention to allow easy access to the specimen for histopathological examination.

It is another object of the invention to eliminate the need of an additional person (other than the surgeon) to put the specimen in place for imaging.

It is another object of the invention to minimize obstruction of the object by overlying structures of the specimen holder.

It is another object of the invention to only minimally interfere with the surgeon's (and other OR personnel's) workflow.

To achieve the above and other objects, the present invention is directed to a sample holder for holding the sample while both the shape of the sample and information about the spatial orientation of the sample with respect to a reference object are preserved. The invention is further directed to an imaging method of using such a sample holder.

In a typical embodiment, the sample holder includes two sets of containers made of low x-ray attenuating materials: a multi-part external container with fixed fiducial markers allowing spatial orientation and a multi-part, movable internal container, also having fiducial markers, with a diameter, e.g., in the range of 2-8 cm that can be freely rotated inside of the external containers in order to match the section plane in which the tissue excision is performed by the surgeon. The easily interpretable externally visible markers allow the surgeon to place the specimen into the specimen holder while preserving information about patient anatomy, e.g., sketches of a patient's position (or anatomical markers of the breast(s) of a patient) on the operating table, or markers with directional information (e.g. superior, inferior, lateral, medial, anterior, posterior, nipple, left, right, etc.) A mechanism can be provided for easy rotation of the internal container relative to the external container to reach the desired orientation, e.g., matching the surgical section plane. A mechanism also can be provided for preservation of the desired orientation. The external container can allow observation of the internal container's polar coordinates (azimuth and polar angle) The internal and external containers allow easy insertion and removal of the specimen.

In typical embodiments, the internal container has two hemispheres that can be opened and securely closed, filled with suitable material, such as a sterile foam or cell-foam (with radio-density lower than that of water) soaked with fixative with appropriate mechanical properties or a sterile gel (with radio-density lower than that of water) with appropriate mechanical properties with its surface delimited by an appropriate thin membrane and allowing the use of fixative on the specimen. The material filling the hemispheres can be provided with a central cavity enabling more stable placement and reduced tissue deformation, where the size of the cavity may be variable in order to match different specimen sizes and shapes. Thus, the shape of the lump can be preserved.

Typical embodiments for fixation of the (movable) internal container include positioning on a ring or hollow cylinder with a diameter smaller than the diameter of the hemispheres, or fixation with pegs.

Typical embodiments of the method include image post-processing methods, such as digital subtraction of images taken with and without the tissue sample.

In a typical embodiment of a method according to the present invention, the object is placed into an object positioning device, the object positioning device is moved into an imaging device, images of the object within the object positioning device are acquired by the imaging device, and the acquired images are stored, processed, or output on a display device, while information about the spatial orientation of the object with respect to a reference object is preserved.

Information about the spatial orientation of the object with respect to the reference object can be displayed on or besides the images taken from the object.

Deformation is preferably minimized if the object is deformable.

The object positioning device can be equipped with positioning markers that enable positioning of the object according to a coordinate system whose frame of reference is given by the reference object. The object positioning device can be equipped with imaging markers that enable the identification of the spatial orientation of the object on the images taken from the object, with respect to a coordinate system whose frame of reference is given by the reference object. The imaging markers or the positioning markers can be visible on the images taken from the object or enable annotations in or besides the images that permit the identification of the spatial orientation of the imaged object with respect to a coordinate system whose frame of reference is given by the reference object.

The object positioning device can have a receptacle for the object to be imaged, where the spatial orientation or position of the receptacle with respect to the remaining parts of the object positioning device (henceforth called "encasement") can be changed. The spatial orientation or position of the receptacle with respect to the encasement can be changed, e.g., for positioning of the object into the receptacle, or fixed, e.g. for imaging. The receptacle can have several parts that allow for fixation of the object between those parts of the receptacle. Parts of the receptacle can be deformable in order to minimize pressure exerted onto the surface of the object, specifically to avoid deformation or damage to the object. The receptacle can be composed of two or more hollow objects, such as hemispheres, which can be filled with deformable material, such as gel protected by a membrane or cell-foam, where the two or more hollow objects can be taken apart, e.g. to enable placement of the object, or can be put together, e.g. to enable imaging in a fixed position. The receptacle can be seated on one or more rings or hollow cylindrical objects whose diameters are smaller or equal than the diameter of the receptacle, e.g. to enable rotation of the receptacle with respect to the encasement. However, any other form of fixation of the receptacle within the encasement may be used, such as pegs.

The object can be a biological organism or a specimen thereof, such as a tissue specimen excised from a living organism, e.g. a human body, or an animal, a plant, or parts thereof. The reference object can be represented by a biological organism, such as a human body, an animal, a plant, or parts thereof.

A human operator, such as a surgeon, radiologist, or pathologist, can place the object into the object positioning device in such a way that information about the spatial orientation of the object with respect to the reference object is preserved. A user can modify the specimen holding device or parts thereof prior to use in order to fit specific needs, e.g., size, weight or other properties of the object to be imaged or preserved, such as by choosing among support pads of different sizes or shapes to be fit into the receptacle in order to provide optimal support of the object.

Images of the object within the object positioning device (with or without information on the spatial orientation of the object with respect to the reference object) can be acquired by one or more of the following imaging methods or devices or by any other suitable imaging methods or devices:

Plain 2D radiography with electromagnetic radiation of any frequency, such as optical (visible) light, infrared, ultraviolet, x-ray, gamma-ray, or particle-based (e.g. radionuclide) imaging, based on physical principles of absorption, emission, diffraction, phase-contrast (including dark-field), or back-scatter, including multiple energy, multiple exposure, charge integration, or photon/particle counting techniques;

Computed tomography with electromagnetic radiation of any frequency, such as optical (visible) light, infrared, ultraviolet, x-ray, gamma-ray, or particle-based (e.g. radionuclide) imaging, based on physical principles of absorption, emission, diffraction, phase-contrast (including dark-field) techniques, or back-scatter, including multiple energy, multiple exposure, charge integration, or photon/particle counting computed tomography techniques;

Any imaging method using scatter grids or exposure control;

Ultrasound imaging, including elastography techniques;

Optical or electron microscopy;

Magnetic resonance imaging without limitation on the choice of pulse sequences;

Optical imaging techniques, including microscopy with electromagnetic radiation or ultrasound of any frequency;

Imaging using material, physical, chemical, or biological processes designed for visualizing or enhancing visualization of the imaged object(s) or parts thereof, such as imaging using contrast agents (e.g. agents used for x-ray techniques including computed tomography, such as iodinated, barium, calcium, gaseous media, noble earths, or any compounds thereof; ultrasound contrast agents, e.g., microbubbles; radionuclides; dyes or stains of any sort, e.g. optical; radionuclides of any sort or compounds of radio-nuclides of any sort; contrast agents used for magnetic resonance imaging including noble earth, e.g. gadolinium, compounds, metal oxides; physical processes used to visualize or enhance visualization of biological processes, such as used in functional or diffusion MRI);

Dynamic imaging of any sort, where more than one image is acquired over time;

Multi-acquisition imaging of any sort where images are acquired over time or simultaneously using different image acquisition methods or different physical/chemical/biological image acquisition parameters; specifically any combination modalities, such as PET/CT, PET/MR, SPECT/CT, SPECT/MRI, PET/MRI, CT/MRI;

Specific imaging modalities: PET, PEM, SPECT, tomosynthesis, magnetic particle imaging; methods or devices for the generation of X-rays that do not require a thermoelectric emission of electrons from a cathode material;

Any form of spectroscopy, e.g. optical or magnetic resonance spectroscopy; and

Combinations of the aforementioned imaging modalities or dynamic, i.e., temporally repeated applications of afore mentioned imaging modalities.

Images of the object within the object positioning device (with or without information on the spatial orientation of the object with respect to the reference object) can be processed by one or more of the following methods or by any other suitable methods:

Digital subtraction, specifically of images taken from the object holding device with and without the object;

Any form of digital or analog image processing, e.g. filtering (e.g. low pass, high pass, band pass), denoising, enhancing, subsampling, color-coding, compression (lossy and lossless);

Image processing of more than one image taken from the object holding device (with or without the object), such as analysis of images over time or pixel/voxel time courses, tomographic reconstruction, image synthesis of more than one image; and Any 3D or 4D (e.g. temporal), or multi-spectral, multimodal, multi-dimensional reconstruction or display technique, such as multi-planar reconstruction, maximum or minimum intensity projection, volume or surface rendering, ray tracing, alpha-blending with and without user interaction.

Images or parts thereof or information on the spatial orientation of the object with respect to the reference object can be stored in any digital form, such as on RAM, hard drives, storage media (e.g. magnetic tapes, CDs, DVDs, solid-state memory), computer networks, e.g. cloud computing, or any analog form, such as printouts of any sort, e.g. on film or paper; and can be stored in any lossy or lossless compressed format. Images or parts thereof or information on the spatial orientation of the object with respect to the reference object can displayed in any way, e.g., as printouts or on computer screens, or where the display can be interactively modified by a user. Images or parts thereof or information on the spatial orientation of the object with respect to the reference object can be stored in DICOM format or are transferred to a computer network, specifically a PACS system. The display of the images or parts thereof or information on the spatial orientation of the object with respect to the reference object is performed on the screen of a viewing station of a PACS system.

Additional markers can be imaged (other than the aforementioned imaging or positioning markers), stored, or displayed, such as length measurement scales or calibration grids.

The object positioning device or parts thereof can be made of a material that is not or almost not visible on the images, e.g., low atomic number material for x-ray techniques (such as various plastic or carbon fiber materials), or diamagnetic materials for MRI. Imaging, positioning, or other markers or parts thereof can be made of material that is clearly visible on the images, e.g., non- or low-radiolucent markers for x-ray methods (e.g. high atomic number materials, such as many metals), para- or ferromagnetic substances for MRI; this includes all sorts of imaging markers currently used in radiology, e.g. fiducial markers used for x-ray diagnostics including mammography, nitroglycerin capsules, lead beads, etc.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

A preferred embodiment of the present invention will be set forth in detail with reference to the drawings, in which like reference numerals refer to like elements or steps throughout.

Figure 1A:
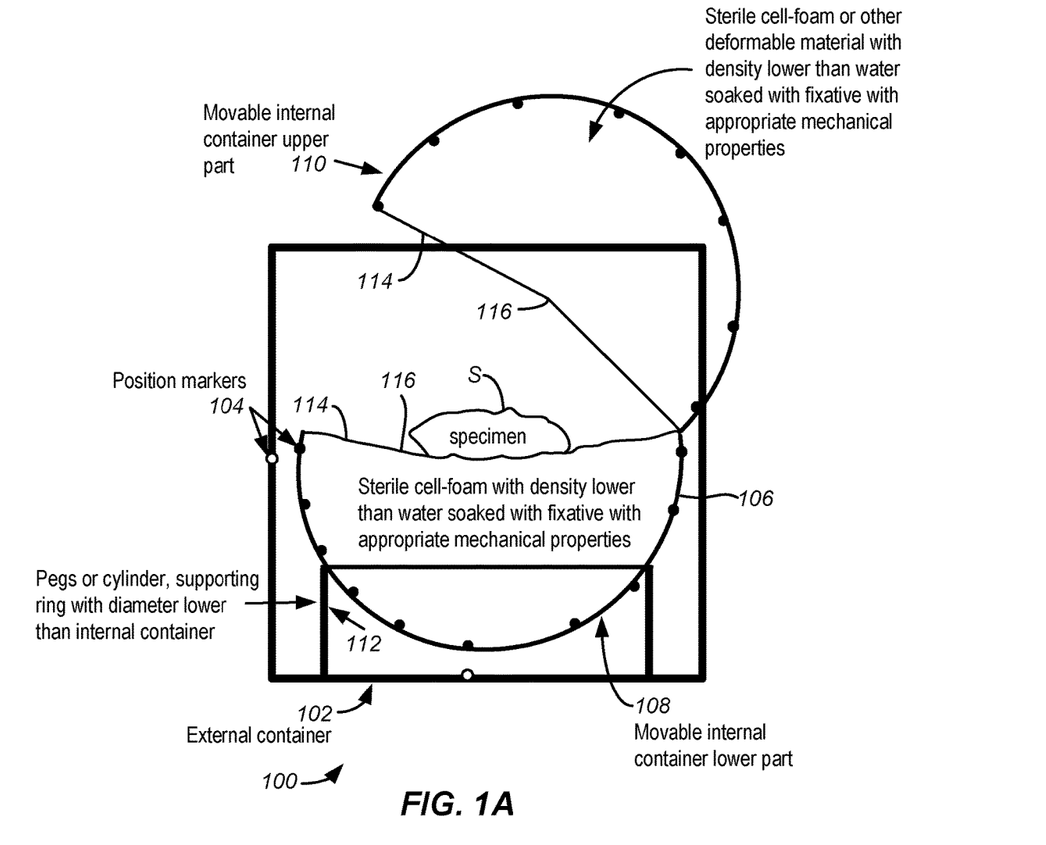
FIGS. 1A and 1B are a cross-sectional view and a perspective view, respectively, showing a specimen holder according to the preferred embodiment.

FIG. 1A is a cross-sectional view showing a lumpectomy specimen holder 100 according to the preferred embodiment. The specimen holder 100 includes an external container 102 with position markers 104. Inside the external container 102 is a spherical internal container 106 having a lower part or hemisphere 108 and an upper part or hemisphere 110, each with position markers 104. The internal container 106 is movable relative to the external container 102 and is supported on a support 112 that can include pegs or a cylinder and a supporting ring with a diameter less than the diameter of the internal container 106. The two parts 108, 110 of the internal container 106 contain a sterile foam 114 or similar deformable material with a density lower than that of water, soaked with a fixative with appropriate mechanical properties. The cell foam 114 has depressions 116 formed therein for receiving a specimen S.

Figure 1B:
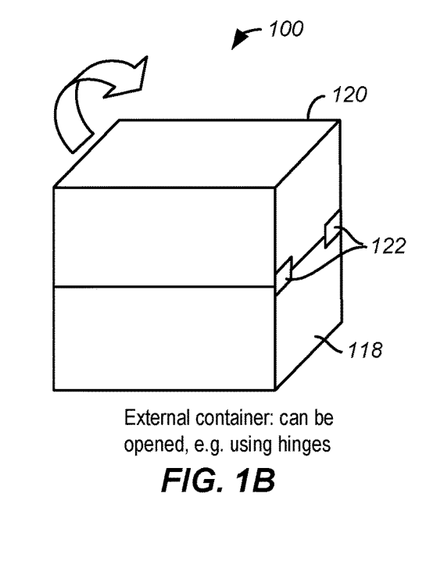

FIG. 1B is a perspective view showing the specimen holder 100. The external container can be formed as two parts 118, 120, connected by hinges 122. A similar hinge can be provided for the internal container 106 (not shown in FIG. 1B). Each of the two parts 118, 120 of the external container can have a support 112 (not shown in FIG. 1B) for stabilizing the internal container 106 to preserve the relative orientation of the two containers 102, 106. Locking can be achieved by using springs or foam between the inner and outer containers. Springs should be positioned so as not to be in the line of sight of either the vertical or the horizontal imaging. Such a locking mechanism can preserve the relative orientation in case the specimen holder 100 is jostled. Locking between the inner and outer container can also be achieved by objects fixed to the inner or outer container, such as pegs or hollow cylinders which prevent relative displacements of the containers with respect to each other by friction. Specifically, such locking may fix the position/orientation of the inner container, when the outer container is closed, while it may allow free displacement or orientation of the internal container with regard to the external container, when the outer container is open. Here, "open" and "closed" refer to an embodiment in which the external container has several components. However, embodiments comprise any mechanism that will allow a user to intentionally fix or release the position or orientation of the inner container in relation to the outer container.

The inner container 106 must be able to close in order to keep the gel or foam 114 in place in any orientation. However, the external container 102 does not need to have a top. It simply needs to be designed to retain the internal container 106 in place. The external container 102 can simply have opposing foam pads on two sides between which the surgeon inserts the inner container 106, against which the foam pads press with enough force to hold the inner container 106 in place but not so much that the inner container 106 cannot be rotated.

In various embodiments, the purpose of the external container 102 can be solely to provide indices 104 indicating position and supporting the inner container 106, or its purpose can include holding the inner container 106 firmly in place.

Figure 5A:
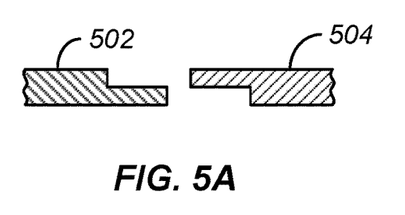
FIGS. 5A and 5B are schematic diagrams showing a frictional engagement between two components of a container.
Figure 5B:
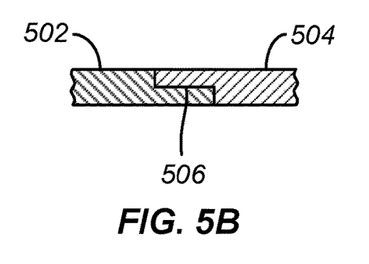

If the external container 102 has two parts 118, 120, it can be hinged, screw together, snap together, have a pressure fit, or have some other mechanism to keep the two parts 118, 120 together. Such mechanisms are known in the container art and will therefore not be disclosed in further detail here, except to note that they should be configured not to interfere with imaging. The two parts 108, 110 of the interior container 106 can close by one of the same mechanisms. One form of frictional engagement that can be used in either container is shown in FIGS. 5A and 5B, in which edges 502 and 504 of a container are formed to interlock and to define a frictional engagement location 506.

The position markers 104 can be on the inside or the outside of each of the external container 102 and the internal container 106, or they can be molded thereinto. They should not obstruct the imaging of the specimen S.

Figure 2:
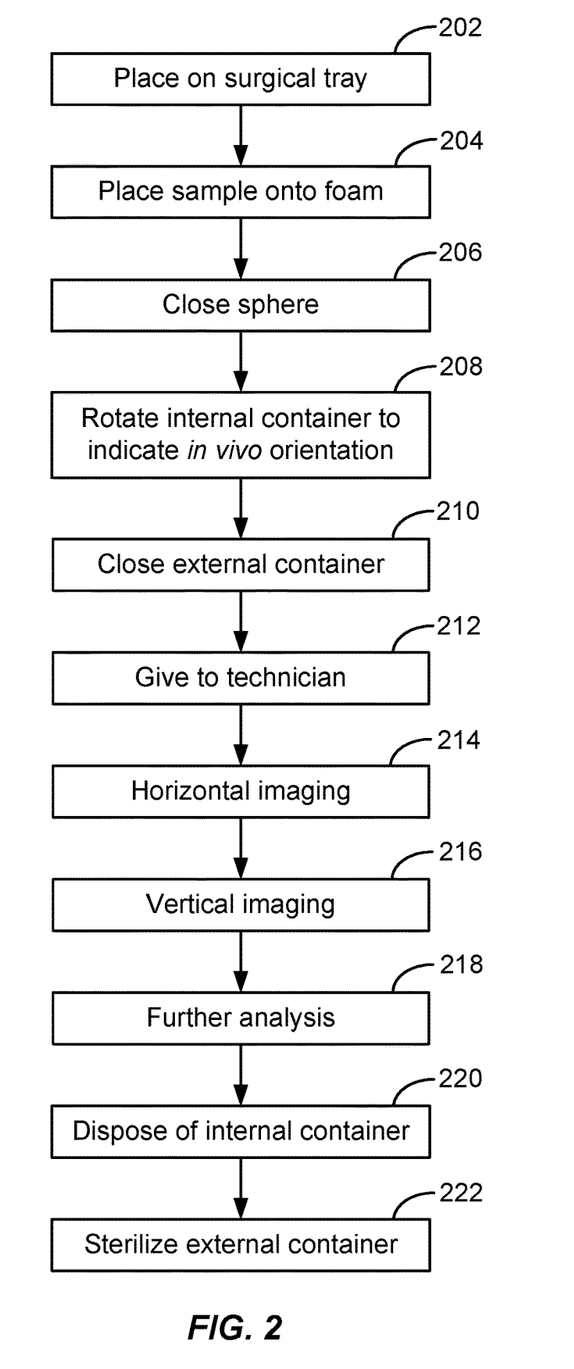
FIG. 2 is a flow chart showing the steps in the use of the specimen holder of FIGS. 1A and 1B.

The use of the specimen holder 100 will be explained with reference to the flow chart of FIG. 2. In step 202, the specimen holder 100 is placed on a surgical tray in the operating room next to the patient. The surgeon places the tissue sample S onto the foam 116 in the lower part 108 of the internal container 106 in step 204 and then joins both sides 110, 108 in step 206 to close the sphere of the internal container 106 without causing deformation of the sample S. The surgeon can then rotate the internal container 106 within the external container 102 in step 208 so that the position markers 104 indicate the orientation in vivo of the specimen S. Diagrams accompanying the specimen holder 100 help the surgeon orient the specimen with respect to patient anatomy. The top half 120 of the external container 102 is closed in step 210, and the specimen holder 100 is handed to the technician in step 212. The technician images the specimen with the closed device in two spatial orientations, horizontal and orthogonal, in steps 214 and 216, respectively. The technician images the horizontal orientation first in step 214 and then rotates the holder 100 by 90 degrees for orthogonal imaging in step 216. The dimensions of the PiXarray imaging surface are 10 cm by 11.2 cm, and the opening is trapezoid-shaped with a bottom base dimension of 21.5 cm and top length of 12.5 cm. Since the specimen holder 100 can be constructed to have a dimension less than 12.5 cm, there should be no difficulty during imaging. After imaging, the specimen holder 100 is taken to pathology, where a pathologist removes the tissue sample S from the specimen holder 100 for further biochemical analysis in step 218. Afterward, the inner container 106 can be disposed of in step 220, while the outer container 102 can be sterilized in step 222 and reused.

The requirements of a specific embodiment for breast lumpectomy will now be disclosed. Those skilled in the art who have reviewed the present disclosure will readily appreciate that other specifics can be used for different uses of the present invention.

Regarding the function of holding the breast tissue, the specimen holder 100 is required to minimize the tissue deformation; the tolerable range is 0-2 mm. It is also required that no sliding of the inner sphere or folding of the tissue occur during the orthogonal imaging. As one of the functional requirements, the specimen holder 100 must allow the surgeon to orient the tissue according to patient anatomy in order to improve the communication between the radiologist and the surgeon about the location of the positive margin. The corresponding performance requirements are to freely adjust the tissue orientation and to clearly indicate the spatial directions. The interior container 106 containing the tissue should be rotatable up to 180 degrees along any axis. Specimen holders 100 for left and right breasts are labeled with six direction markers (medial/lateral, anterior/posterior, superior/inferior) that can be shown in the image; they can also be labeled, possibly with other markers visible in the image, to identify them as for the left or right breast. Another performance requirement is that the device be closed shut when it is transferred from the operating room to the PiXarray and when the two spatial images are taken, meaning that no person other than the surgeon can directly handle the tissue specimen during the process. To be imaged by the PiXarray, the device is required to be compatible with mammography, maintaining a resolution that provides clear differentiation between the tumor and the tumor-free margin.

Interface requirements specify the device characteristics mandated by the external system. The dimensions of the external container 102 and of the internal container 106 are constrained by the size of the excised breast tissue and the imaging area of the PiXarray 100. The specifications of the supporting rings are determined based on the tissue size, the sphere diameter and box height.

The materials of the specimen holder 100, apart from the position markers 104, should be radiolucent, so that it will not interfere with the image of the tissue, but the position markers 104 should be visible on the images. A preferred material for the radiolucent components is polycarbonate. The materials of the external container 102, the internal container 106, and the foam 114 need to be light, so that tissue deformation can be minimized. The number of steps required to handle the specimen container 100 must be minimal. To use the specimen container 100 in an operating room, it must be sterilized.

Based on the above requirements, the specifications, metrics and associated testing plans have been determined.

The typical diameter of the excised breast tissue during the lumpectomy procedure is within 0.3 to 6 cm. Therefore, fixing the maximum tissue size to be 6 cm requires the diameter of the internal container 106 to be larger than 6 cm. To compensate for irregular boundaries that may occur in a realistic surgical setting, the diameter of the internal container 106 should be at least 8 cm. To provide a 2 cm clearance between the internal and external containers, the external container 102 is formed as a 12 cm cube. The internal container 106 is within the PiXarray imaging area, while the external container 102 is outside.

To be able to hold each hemisphere 108 or 110, the ring of each support 112 needs to have a diameter smaller than that of the internal container 106. To prevent the ring from interfering with the tissue on the image, the ring must be larger than the tissue in diameter. The height of the rings must be appropriately designed so that the internal container 106 can be securely held and the exterior container 102 can be closed shut. If the lower ring is able to hold the lower hemisphere 108 5 mm higher than the bottom part 118 of the exterior container 102, then the side walls of the box will not prevent the surgeon from easily placing the tissue sample S onto the hemisphere 108. The lower support has a diameter of 7 cm and a height of 4.36 cm; the upper support has a diameter of 7 cm and a height of 3.35 cm.

Figure 3:
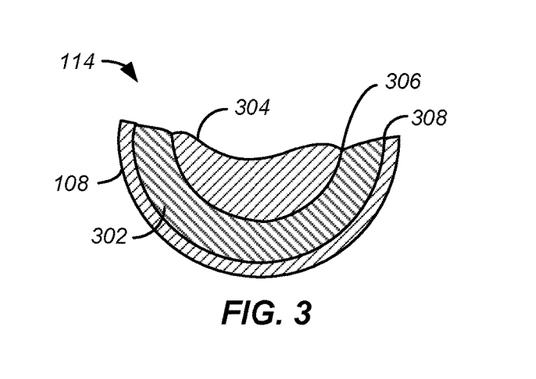
FIG. 3 is a cross-sectional view showing the configuration of the sterile foam used in specimen holder of FIGS. 1A and 1B.

As shown in FIG. 3, the foam 114 comprises a low-density, radiolucent foam 302 for the stabilizing material in the interior container 106. The foam 302 is constructed into a ring that fits within the hemisphere 108, with the top edge just barely meeting the surface of the hemisphere. On top of that ring 302 sits another, thinner piece of softer foam 304, which supports the tissue specimen and conforms to the shape of the tissue. The ring of foam 302 underneath the top layer 304 allows for larger specimens to sink down into the hemisphere 108 and minimize the compression and deformation of the specimen. The layers 302, 304 of the foam are attached to each other using radiolucent plastic thread 306. The entire foam structure 302, 304 is attached to the hemisphere 108 using radiolucent silicone glue 308.

Figure 4:
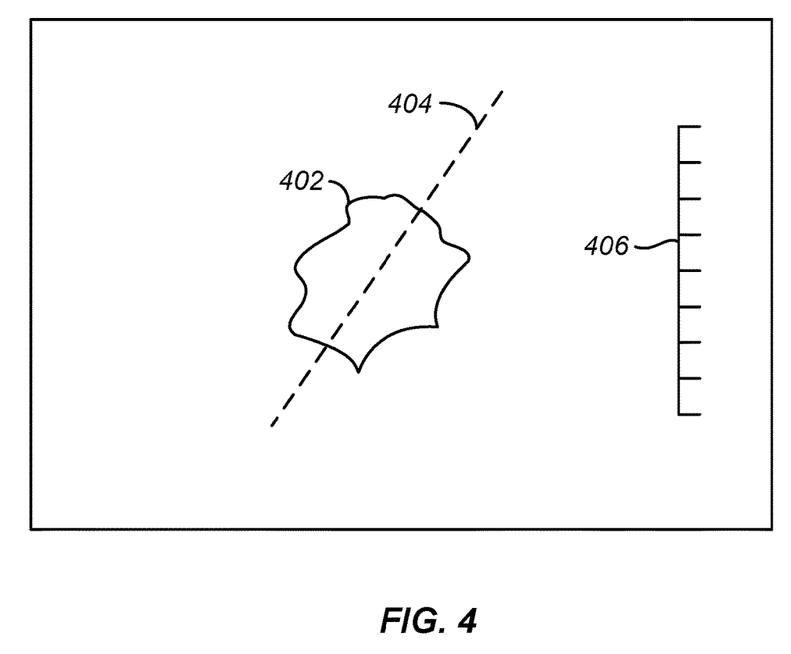
FIG. 4 is an example of an image produced in accordance with the preferred embodiment.

FIG. 4 shows an example of an image 400. The image 400 includes an image 402 of the tissue sample S with an annotation 404 showing the orientation of the tissue sample S relative to the reference object. The image 400 also includes a scale 406, which may be generated through scale markers on the specimen holder 100, generated through a scale separately provided in the path of imaging radiation, or computer generated.

While a preferred embodiment for breast lumpectomy has been set forth in detail above, those skilled in the art who have reviewed the present disclosure will readily appreciate that other embodiments can be realized within the scope of the present invention. For example, the dimensions can be varied to suit both the tissue or other object to be imaged and the imaging device into which the specimen holder is to be placed. Also, disclosures of materials are illustrative rather than limiting, as any material having suitable properties can be used. Furthermore, the object can be from a human being, a non-human animal, any other organism, or a non-biological source. Moreover, the external container may have a cylindrical shape, i.e., a circular rather than rectangular base, thus allowing specimen holding devices that fit into the gantry of (Micro-) CT or MR devices without dead space. Thus, larger tissue samples can be imaged. Therefore, the present invention should be construed as limited only by the appended claims.

What is claimed is:

1. An object positioning device for preserving an object for imaging having a length, a width, and a thickness, while preserving a shape and a spatial orientation of the object for imaging relative to a reference object, the device comprising:
    a first container for holding the object for imaging while preserving the shape of the object for imaging, which container can close and which encloses on all sides the object for imaging when closed;
    two or more fiducial marks on the container for identifying the three dimensional spatial orientation of the object for imaging relative to the reference object during the imaging, and
    a deformable material for receiving and holding the object for imaging in position along its length and width with minimal deformation when said object for imaging is placed into said device.

2. The device of claim 1, said deformable material for receiving and holding the object for imaging encloses said object for imaging on all sides when said first container is closed.

3. The device of claim 1, wherein the deformable material comprises a foam.

4. The device of claim 1, wherein the deformable material comprises a cell foam.

5. The device of claim 1, wherein the deformable material comprises a gel separated from the detached object by a membrane.

6. The device of claim 1, wherein the deformable material has a cavity formed therein for receiving the object for imaging.

7. The device of claim 1, wherein the first container is an internal container disposed within a second, exterior container, and wherein the fiducial marks are disposed on the interior container, the exterior container, or both.

8. The device of claim 7, wherein the interior container is mounted in the exterior container to be rotatable within the exterior container.

9. The device of claim 8, wherein the exterior container comprises a ring-shaped or cylindrical mount on which the interior container is placed.

10. The device of claim 7, wherein the interior container comprises two hemispherical components.

11. The device of claim 1, wherein the container comprises a material with a first x-ray attenuation, and wherein the fiducial marks comprise a material with a second x-ray attenuation that is higher than the first x-ray attenuation.

12. The device of claim 1, wherein the container comprises a diamagnetic material, and wherein the fiducial marks comprise a paramagnetic or ferromagnetic material.

13. A method for forming an image of a detached object having a length, width, and thickness while preserving a shape and a spatial orientation of the detached object relative to a reference object, the method comprising:
    (a) placing the detached object into an object positioning device that comprises (i) a first container for holding the detached object while preserving the shape of the detached object, (ii) fiducial marks on the first container for identifying the spatial orientation of the detached object relative to the reference object during the imaging, and (iii) a deformable material for receiving and holding the detached object in position along its length and width with minimal deformation when said detached object is placed into said object positioning device;
    (b) placing the object positioning device into an imaging device; and
    (c) imaging the detached object and the object positioning device to form the image.

14. The method of claim 13, wherein the deformable material for receiving and holding the detached object does not deform the detached object.

15. The method of claim 14, wherein the deformable material comprises a foam.

16. The method of claim 14, wherein the deformable material comprises a cell foam.

17. The method of claim 14, wherein the deformable material comprises a gel.

18. The method of claim 13, wherein the deformable material has a cavity formed therein for receiving the detached object.

19. The method of claim 13, wherein the object positioning device further comprises a second container exterior to said first container, and wherein the fiducial marks are disposed on both the first, interior container and the second, exterior container.

20. The method of claim 19, wherein the first, interior container is mounted in the second, exterior container to be rotatable within the exterior container, and wherein step (a) comprises rotating the interior container relative to the exterior container such that a relative orientation of the fiducial marks on the interior container and the fiducial marks on the exterior container represents the spatial orientation of the object relative to the reference object.

21. The method of claim 20, wherein the exterior container comprises a ring-shaped or cylindrical mount on which the interior container is placed.

22. The method of claim 19, wherein the interior container comprises two hemispherical components.

23. The method of claim 13, wherein the container comprises a material with a first x-ray attenuation, and wherein the fiducial marks comprise a material with a second x-ray attenuation that is higher than the first x-ray attenuation.

24. The method of claim 13, wherein the container comprises a diamagnetic material, and wherein the fiducial marks comprise a paramagnetic or ferromagnetic material.

25. The method of claim 13, wherein step (c) further comprises displaying information about the spatial orientation of the detached object relative to the reference object on or beside the image.

26. The method of claim 13, Wherein step (a) comprises placing the object into the object positioning device to minimize deformation of the detached object.

27. The method Of claim 13, wherein step (c) further comprises using the fiducial marks to poisition the detached object according to a coordinate system whose frame of reference is given by the reference object.

28. The method of claim 27, wherein step (c) further comprises using the fiducial marks to identify the spatial orientation of the detached object on the image with respect to the coordinate system.

29. The method of claim. 27, wherein step (c) further comprises providing annotations in or besides the image that permit the identification of the spatial orientation of the detached object with respect to the coordinate system.

30. The method of claim 13, wherein the detached object is a biological organism a specimen of a biological organism.

31. The method of claim 30, wherein the detached object is a tissue specimen excised from a living organism.

32. The method of claim 31, wherein the reference object is the biological organism.

33. The method of claim 13, wherein, in step (a), a human operator places the detached object into the object positioning device in such a way that information about the spatial orientation of the detached object with respect to the reference object is preserved.

34. The method of claim 13, wherein step (a) comprises selecting from among support elements of different sizes or shapes in order to provide optimal support of the detached object.

35. The method of claim 13, wherein step (c) is performed using one of:
  (i) two-dimensional radiography;
  (ii) computed tomography;
  (iii) an imaging method using scatter grids or exposure control;
  (iv) ultrasound imaging;
  (v) optical microscopy;
  (vi) electron microscopy;
  (vii) magnetic resonance imaging;
  (viii) optical imaging;
  (ix) imaging using material, physical, chemical, or biological processes designed to visualize or enhance visualization of the detached object or parts of the detached object;
  (x) dynamic imaging;
  (xi) multi-acquisition imaging;
  (xii) x-ray imaging;
  (xiii) spectroscopy; and
  (xiv) a combination of the above.

36. The method of claim 13, further comprising a step of image processing comprising one of:
  (i) digital subtraction;
  (ii) digital or analog image processing;
  (iii) image processing of more than one image taken from the object positioning device both with and without the detached object; and
  (iv) three- or four-dimensional reconstruction or display.

37. The method of claim 13, further comprising storing the image in a persistent digital storage medium.

38. The method of cairn 13, further comprising displaying the image.

39. The method of claim 38, wherein the image or a part the image or the information on the spatial orientation of the detached object with respect to the reference object is displayed on a screen or a viewing station of a PACS system.

40. The method of claim 13, further comprising storing the image or a part of the image or information on the spatial orientation of the object with respect to the reference object in DICOM format.

41. The method of claim 13, further comprising transferring the image to a computer network.

42. The method of claim 41 wherein the computer network is a PACS system.

43. The method of claim 13, where additional markers are imaged (other than aforementioned imaging or positioning markers), stored, or displayed.

44. The method of claim 43, wherein the additional markers comprise length measurement scales or calibration grids.

* * * * *